United States Patent [19]

Fujita et al.

[11] Patent Number: 4,904,803

[45] Date of Patent: Feb. 27, 1990

[54] PROCESS FOR PRODUCING N-SUBSTITUTED MALEIMIDES

[75] Inventors: Takeyuki Fujita, Yokosuka; Tuyoshi Irie, Kobe; Yasuyuki Takayanagi, Yokohama; Takeshi Narita, Yokohama; Yuya Yano, Yokohama, all of Japan

[73] Assignees: Nitto Chemical Industry Co., Ltd.; Mitsubishi Rayon Co., Ltd., both of Tokyo, Japan

[21] Appl. No.: 310,921

[22] Filed: Feb. 16, 1989

[30] Foreign Application Priority Data

Feb. 25, 1988 [JP] Japan ................................. 63-40773
Feb. 25, 1988 [JP] Japan ................................. 63-40774
May 10, 1988 [JP] Japan ................................. 63-111540

[51] Int. Cl.$^4$ .............. C07D 207/448; C07D 207/452
[52] U.S. Cl. ...................................... 548/548; 548/549
[58] Field of Search ............................... 548/548, 549

[56] References Cited

FOREIGN PATENT DOCUMENTS 61-229862 10/1986 Japan .
62-138468 6/1987 Japan .

OTHER PUBLICATIONS

C. A., Bd. 106, 1987, 119465 c.
C. A., Bd. 107, 1987, 58847 a.
C. A.=Chemical Abstracts, Bd. 103, 1985, 215157 n.
C. A., Bd. 1986, 34000 f.
C. A., Bd. 104, 1986, 207144 m.

*Primary Examiner*—David B. Springer
*Attorney, Agent, or Firm*—Oblon, Spivak, McClelland, Maier & Neustadt

[57] ABSTRACT

N-substituted maleimides are prepared by reacting maleic anhydride with an amine in the presence of Cu or a copper compound and purifying the maleimide produced in the absence of presence of said Cu or copper compound. N-substituted maleimides are widely useful or starting materials or intermediates for medicines, agricultural chemicals, dyes, macromolecular compounds, and the like.

13 Claims, No Drawings

PROCESS FOR PRODUCING N-SUBSTITUTED MALEIMIDES

BACKGROUND OF THE INVENTION

1. Field of the Invention

The present invention relates to a process for producing N-substituted maleimides. More specifically, the invention relates to (i) a process for producing N-substituted maleimides which comprises subjecting either maleic anhydride and an amine or a maleic acid monoamide, which is produced from the above two compounds, to dehydrating reaction or dehydration ring closure in an organic solvent in the presence of a catalyst and (ii) a process for purifying N-substituted maleimides which comprises washing the reaction product mixture obtained by the above process (i) or a prior art process and isolating the intended pure product from the washed mixture.

N-Substituted maleimides have a wide variety of applications as starting materials or intermediates for medicines, agricultural chemicals, dyes, macromolecular compounds, etc.

2. Description of the Prior Art

Various processes of the prior art are known for producing N-substituted maleimides. An example of the known processes comprises the dehydration ring closure of a maleic acid monoamide (a maleamic acid), which is readily producible from maleic anhydride and an amine, by heating at 180° C. (L.E. Coleman et al., J. Org. Chem., 24, 135-136 (1959)). According to this process, however, the yield of the intended N-substituted maleimide is as low as 15-50%.

There is also a process, well known as a laboratory method, which comprises reacting maleic anhydride with aniline using a dehydrating agent such as acetic anhydride in the presence of a sodium acetate catalyst (Org. Synth. Coll., 5, 944 (1973)). This process, although relatively-high yields of N-substituted maleimides are obtainable thereby, has a drawback in that since the dehydrating agent needs to be used in a stoichiometric amount, the production is made expensive by the additional cost of this auxiliary material. Hence this process is unfitted for industrial production.

On the other hand, there is a process conceivable to be advantageous industrially which comprises the dehydration ring closure of a maleic acid monoamide under mild conditions wherein no dehydrating agent but an effective dehydration catalyst is used. A number of such processes are proposed, including a process employing an acidic catalyst such as sulfuric acid or sulfonic acid (British Pat. No. 1,041,027), a process employing a basic catalyst such as sodium hydroxide or triethylamine (Japanese Pat. Publication No. Sho. 47-24024, corresponding to Canadian Pat. No. 906,494 and German Pat. No. 2,100,080), and a process employing a heterogeneous catalyst such as an ion-exchange resin (Japanese Pat. Application Kokai No. Sho. 61-85359, corresponding to European Pat. No. 0,177,031 B1). According to these processes, the reaction yield (conversion to product) reaches 90% or more but the inhibition of side reaction is still insufficient; hence the reaction product mixtures contain such impurities as unreacted materials, intermediates, and various by-products and polymers, besides catalysts.

It is necessary to remove impurities sufficiently from N-substituted maleimides since these compounds are used as materials for medicines, agricultural chemicals, polymers, etc.

For the purification of N-substituted maleimides, there are proposed methods, for example, one comprising pouring the reaction product solution into a large amount of cold water, filtering the formed crystals, and further washing them with a large amount of water or organic solvent (Organic Synthesis Coll., 5, 44 (1973)); one comprising neutralizing and washing the reaction product solution with a dilute aqueous sodium carbonate solution or the like, separating the washed organic layer, and removing the solvent therefrom by distillation (Japanese Pat. Publication No. Sho. 61-204166, corresponding to U.S. Pat. No. 4,623,734); those comprising treating the reaction product solution with a strong acid such as sulfuric acid to convert by-products into resinous matter removing it, and washing the residual solution (Japanese Pat. application Kokai Nos. Sho. 61-22065 and Sho. 61-204166, corresponding to U.S. Pat. No. 4,623,734); and one comprising washing the reaction product solution with a dilute aqueous alkali solution, further washing it with water, removing the solvent by distillation, and recrystallizing the residue from an alcoholic solvent (Japanese Pat. application Kokai No. Sho. 60-10054). However, such methods as illustrated above are disadvantageous in that since the by-product formed in the step of imidization through dehydration ring closure is also insoluble in water, it is impossible to remove this by-product sufficiently by washing with water and hence a high-purity N-substituted maleimide is difficult to obtain and moreover an emulsion layer and/or a precipitate forms between the aqueous layer and the organic layer which result from the wash with water, thus worsening the separability of by-product. This is attributable to the low selectivity of the imidization through dehydration ring closure, that is, a side reaction occurring during the imidization yields a by-product having an emulsifying action or a by-product scarcely soluble in water as well as in the used organic solvent. Accordingly, when the separated organic solution containing such a by-product is subjected, as it is, to an isolation procedure such as distillation, polymerization tends to occur simultaneously and hence the yield and the purity lower. In order to avoid this, it is necessary that the organic layer and the aqueous layer, before their separation from each other, be left standing for a very long time (e.g., about two to twenty hours) and the still remaining emulsion layer be removed or that the destruction of emulsion layer and the removal of insoluble matter be forced by ultracentrifugation, filtration, or other procedure. This makes the washing step complicated and bothersome. The recrystallization from an alcohol also causes a side reaction with the alcohol or is accompanied by polymerization. Therefore it is difficult to recover a high-purity product in a high yield by this recrystallization.

On the other hand, the purification of N-substituted maleimides by distillation is also proposed (Japanese Pat. application Kokai Nos. Sho. 60-112758 and Sho. 60-112759). However, maleimides, having ethylenic double bonds, tend to polymerize upon heating in the distillation and this lowers the distillation yield. To prevent the yield drop due to such polymerization in the distillation, there are proposed methods of conducting the distillation in the presence of a stabilizer or polymerization inhibitor (Japanese Pat. application Kokai No. Sho. 61-229862, corresponding to U.S. Pat. No. 4,623,734) or conducting the distillation after neutralization of the product solution with an alkaline earth metal compound (Japanese Pat. application Kokai No. Sho. 62-138468). But the complete prevention of the polymerization cannot yet be achieved according to these methods.

As stated above, the prior techniques of purification are insufficient in the removal of impurities including by-products or in the prevention of the polymerization accompanying the distillation, hence involving problems in the yield and purity of product. Hence these techniques are still unsatisfactory for commercial production.

SUMMARY OF THE INVENTION

The first object of the present invention is to establish a process for producing N-substituted maleimides which solves problems of the prior art process for producing the same and can be operated industrially to advantage. More specifically, the first object is to establish a process for producing the same, in which the selectivity of reaction is improved to prevent the formation of any by-product responsible for worsening the separability of the washed organic layer, whereby the polymerization occurrence in the purification step is prevented and thus N-substituted maleimides of high purity can be obtained in high yields.

As a result of intensive studies the present inventors have found that N-substituted maleimides of high purity can be obtained in high yields without causing the incidental formation of insoluble matter or of the emulsion layer by a very simple process wherein, maleic anhydride is imidized with a primary amine or a maleic acid monoamide produced from the above two compounds is imidized through dehydrating reaction or dehydration ring closure in the presence of at least one of copper and copper compounds, the reaction product mixture is neutralized and washed with water and the product is isolated from the washed mixture. Thus the first aspect of the present invention has been accomplished.

The second object of the present invention is to provide a process for purifying N-substituted maleimides which solves problems in the prior art process for purifying the same and can be operated industrially to advantage. More specifically, the second object is to provide a process for purifying the same, in which impurities including by-products are removed sufficiently from a crude N-substituted maleimide and its polymerization during distillation is prevented, whereby the intended high-purity N-substituted maleimide can be obtained in a high yield.

The present inventors have found that high-purity N-substituted maleimides can be obtained in high yields by a process comprising washing a reaction product mixture which contains an N-substituted maleimide and, if necessary, subjecting the washed mixture to distillation in the presence of a phosphorus oxyacid. Thus the second aspect of the present invention has been accomplished.

DETAILED DESCRIPTION OF PREFERRED EMBODIMENT

The first aspect of the present invention is a process for producing N-substituted maleimides which comprises the steps of subjecting maleic anhydride and an aromatic or aliphatic primary amine to dehydrating reaction by heating them in an organic solvent in the presence of a catalyst and at least one of copper and copper compounds to synthesize an N-substituted maleimide, washing the reaction product mixture with at least one liquid selected from a dilute aqueous alkali solution, water, and a dilute aqueous acid solution, and isolating the N-substituted maleimide from the washed organic layer.

In the above process, the N-substituted maleimide may be synthesized from maleic anhydride and an aromatic or aliphatic primary amine either directly in one stage by heating to cause the dehydrating reaction or indirectly in two stages by preparing once a maleic acid monoamide and then heating it to cause the dehydration ring closure, in an organic solvent in the presence of a catalyst and at least one of copper and copper compounds.

Hereinafter, embodiments of the present invention are described.

Maleic anhydride, used as a starting material in the invention, may be supplied from any source. It is convenient to use a suitable one selected from commercially available grades of maleic anhydride. The use of maleic acid instead of maleic anhydride is not advisable from the viewpoint of reactivity and economy, though the reaction in this case proceeds similarly. As regards the primary amide used as another starting material, suitable aromatic primary amines include, for example, aniline, naphthylamine, toluidine, xylidine, chloroaniline, dichloroaniline, hydroxyaniline, nitroaniline, and phenylenediamine. Of these amines, preferred are aniline, toluidine, chloroaniline, dichloroaniline, hydroxyaniline, and nitroaniline. Suitable aliphatic primary amines include, for example, methylamine, ethylamine, propylamine, butylamine, pentylamine, cyclohexylamine, allylamine, and ethylenediamine, of which preferred are methylamine, butylamine, and cylohexylamine. Maleic anhydride is used in an amount desirably from 0.8 to 1.5 moles, preferably from 0.9 to 1.2 moles, per mole of the primary amine.

The dehydrating reaction or dehydration ring closure in the present invention is carried out in an organic solvent in the presence of a catalyst and at least one of copper and copper compounds.

That is, the first aspect of the invention comprises heating maleic anhydride and the above-cited aromatic or aliphatic primary amine in an organic solvent in the presence of a catalyst and at least one of copper and copper compounds. This reaction can be conducted according to various procedures. In view of the workability and other factors, preferred is the following procedure: Predetermined amounts of maleic anhydride, primary amine, organic solvent, copper or copper compound, and catalyst are charged into a reactor, and heated to a given temperature to carry out the reaction or predetermined amounts of maleic anhydride, organic solvent, copper or copper compound, and catalyst are charged into a reactor, and heated to a given temperature, and then a predetermined amount of primary amine is added gradually to carry out the reaction.

The organic solvent used in the process of the present invention may be any of those which dissolve maleic anhydride, the aromatic or aliphatic primary amine, and the maleic acid monoamide and do not undergo any change in the reaction. Of such solvents, preferred are aromatic hydrocarbons including benzene, toluene, xylene, ethylbenzene, styrene, and cumene. In particular, benzene, toluene, and xylene are preferable.

There is no particular restriction on the amount of organic solvent to be used. Considering the workability and economy, however, the organic solvent is preferably used in such an amount that the product concentration therein may be about 10–60%, particularly about 15–35%. The reaction can be accelerated by using a mixture of the above aromatic hydrocarbon solvent with an aprotic polar solvent. Such aprotic polar solvents include, for example, formamide, N-methylformamide, dimethylformamide, dimethylacetamide, dimethylsulfoxide, sulfolane, γ-butyroloctone, and hexamethylphosphorotriamide. Of these solvents, preferred are dimethylformamide, dimethylacetamide, and dimethylsulfoxide.

The amount of aprotic polar solvent to be used is optional, but usually up to 50%, preferably about 0.5–25%, of the total amount of solvents.

The copper or copper compound used in the process of the present invention exhibits the action of improving the reaction selectivity and inhibiting the formation of a by-product which is responsible for worsening the separability of the aqueous layer resulting from the wash in the purification step. Examples of the copper or copper compound are; metallic copper in powder or foil form; inorganic copper compounds including cuprous oxide, cupric oxide, copper hydroxide, copper sulfide, cuprous chloride, cupric chloride, copper sulfate, copper nitrate, and copper phosphate; and organic copper complex compounds including copper bis(acetylacetonate) and copper ethylenediaminetetraacetate. In view of the heat stability and economy, metallic copper and inorganic copper compounds are preferable. These copper and copper compounds may be used alone or in combination.

There is no particular restriction also on the amount of copper or copper compound to be used, but preferred amounts thereof are generally from 5 ppm to 5% by weight based on the reaction fluid. The amount can be reduced by the joint use of the above-cited aprotic polar solvent.

Suitable catalysts for use in the process of the present invention include; inorganic acids, e.g. sulfuric acid, sulfurous acid, sulfuric anhydride, phosphoric acid, phosphorous acid, and polyphosphoric acid; organic acids, e.g. benzenesulfonic acid, toluene-sulfonic acid, benzenephosphonic acid, trichloroacetic acid, and trifluoroacetic acid; organic bases, e.g. triethylamine, pyridine, dimethylaniline, and sodium acetate; and ion-exchange resins of the strong-acidic type, weak-acidic type, and weak-basic type. Of these catalysts, preferred are sulfuric acid, phosphoric acid, benzenesulfonic acid, toluenesulfonic acid, and ion-exchange resins. There is no particular restriction on the amount of catalyst to be used, but it is preferably used in an amount of 0.05 to 40%, particularly 0.2 to 25%, by weight based on the reaction fluid.

The reaction temperature in the process of the present invention is generally from 50° to 200° C., preferably from 70° to 160° C. There is no particular restriction on the reaction pressure, which can be chosen widely from reduced, normal, and elevated pressures. The reaction period is generally from 0.5 to 10 hours depending on conditions such as raw material concentrations, amount of catalyst, kind of solvent, and reaction temperature.

The thus obtained reaction product solution containing an N-substituted maleimide is first washed and then the resulting organic layer is purified to isolate the N-substituted maleimide.

In the present invention, the product solution is washed once or more with at least one of a dilute aqueous alkali solution, water, and a dilute aqueous acid solution. Dilute aqueous solutions of suitable alkali compounds include those of hydroxides, carbonates, and hydrogen carbonates of alkali metals and of alkaline earth metals. Of these compounds, preferred are sodium hydroxide, carbonate, and hydrogencarbonate, and potassium hydroxide, carbonate, and hydrogencarbonate. Dilute aqueous solutions of suitable acids include those of sulfuric acid, sulfurous acid, phosphoric acid, phosphorous acid, hydrochloric acid, benzenesulfonic acid, and toluenesulfonic acids, of which preferred are sulfuric acid and phosphoric acid. It is more favorable to wash with a dilute aqueous solution of such alkali and then with a dilute aqueous solution of such acid.

There is no particular restriction on the amounts of dilute aqueous alkali solution, water, and dilute aqueous acid solution to be used, but preferred amounts thereof are about 10 to 100% of the amount of reaction product mixture to wash. The amount and the pH of wash liquid are chosen so that the pH of the aqueous solution after washing may be in the range of 0.5 to 8, preferably 1.5 to 7. The wash temperature is from 20° to 90° C., preferably from 30° to 70° C.

The washing procedure is as follows: Said wash liquid is added to the reaction product solution and these liquids are stirred for a period of 5 to 60 minutes. The resulting mixture is left standing to separate into two layers. According to the prior art process, this separation is worse remarkably, that is, a heterogeneous layer containing large amounts of emulsion and insoluble matter forms between the two layers. In order to better the separation, the prior art needs therefore to last the standing for about two to twenty hours or to separate the emulsion and insoluble matter forcibly by ultracentrifugation, filtration, or the like. According to the process of the first aspect of the present invention, the stirred mixture, on the contrary, separates into two layers completely in an extremely short time (usually in 30 minutes) and hence not only the workability is better outstandingly but also an organic layer contaminated with much less impurities can be obtained in a high yield. If necessary, copper or the above-mentioned copper compound may be further added since it has an action favoring the separability of the aqueous washing layer.

Then the N-substituted maleimide in the organic layer obtained by the above washing procedure is isolated according to the known recrystallization or distillation method.

In the recrystallization method, it is advisable to crystallize and separate the product by using an alcoholic solvent such as methanol, ethanol, or isopropanol or an aromatic hydrocarbon solvent such as benzene, toluene, xylene, or styrene.

In the distillation method, it is advisable to carry out the distillation under normal or reduced pressure. Since N-substituted maleimides have tendencies to polymerize, the distillation is conducted desirably at a temperature as low as possible and under a reduced pressure generally up to 20 mm Hg, preferably up to 10 mm Hg. It may be noted that the distillation in the presence of a phosphorus oxyacid produces favorable effects.

When a maleic acid monoamide produced by reacting maleic anhydride with an aromatic or aliphatic primary amine is subjected to dehydration ring closure as stated before, this reaction can be carried out without isolating the maleic acid monoamide.

Said synthetic reaction for a maleic acid monoamide is desirably carried out in an organic solvent such as the above-mentioned aromatic hydrocarbon solvent or a mixture thereof with an aprotic polar solvent. This reaction readily proceeds at temperatures up to about 150° C. without special use of catalyst. Suitable reaction temperatures are from ambient to 100° C. Suitable reaction periods are from 0.5 to 24 hours depending on the reaction temperature, the solvent used, etc.

The wash of the product solution resulting from the dehydration ring closure and the isolation of N-substituted maleimide can be carried out in the same manner as in the purification of the product solution resulting from the one-stage synthesis.

Because both a raw material and the product in the process of the present invention have polymerization-active double bonds, the use of a polymerization inhibitor in the reaction step as well as in the purification step is effective and never detracts the effect of the present invention. Such effective polymerization inhibitors include hydroquinone, methoxyphenol, t-butylcatechol, phenothiazine, thiourea, hydroxyquinoline, cupferron, and N-nitrosodiphenylamine.

The purification process according to the second aspect of the present invention may be applied to crude N-substituted maleimides obtained by synthetic methods other than the method used in the production process according to the first aspect of the invention. That is, the present purification process is also applicable to crude N-substituted maleimides obtained by carrying out the reaction in the presence of such a catalyst as stated above and in the absence of copper or any copper compound.

In the latter case, however, it is essential to remove the impurities contained in the reaction product solution by filtration and allow to stand the solution for at least 2 hours after the completion of the reaction before the solution is subjected to the present purification process as discussed hereinbefore. Such steps definitely increases the production cost when compared with that of the process of the first aspect of the present invention, though.

In the production of N-substituted maleimides by these other synthetic methods, the above-cited polymerization inhibitor can also be used favorably without producing any adverse effect.

The N-substituted maleimide-containing product solution obtained by such a known synthetic method as stated above that is different from the method of the present invention is purified by washing first, followed by distillation, if necessary, in the presence of a phosphorus oxyacid.

The wash is carried out at least once with one or more of a dilute aqueous alkali solution, water, and a dilute aqueous acid solution. Preferably, the reaction mixture is washed first with a dilute aqueous alkali solution, and then, if necessary, washed again once or more with water and a dilute aqueous acid solution. It is preferable in particular to wash the mixture with a dilute aqueous alkali solution and then with a dilute aqueous acid solution. The wash is desirably conducted so that the pH of the aqueous layer formed after this wash may be in the range of 0.5 to 8.

While dilute aqueous solutions of various alkali compounds can be used for the wash, those of hydroxides, carbonates, and hydrogencarbonates of sodium and potassium are preferable for the wash in view of the washing performance, washing workability, and economy. Suitable concentrations of the dilute aqueous alkali solution are from 1 to 20% by weight.

While dilute aqueous solutions of various acids can also be used for the wash, those of sulfuric acid and phosphoric acid are preferable for the wash in view of the washing performance, washing workability, and economy. Suitable concentrations of the dilute aqueous acid solution are such that the pH of the solution may be in the range of 0.1 to 5. There is no particular restriction on the amount of each liquid to be used for the wash, but preferred amounts thereof are about 10–100% of the amount of the reaction product solution. The wash temperature is from 20° to 90° C., preferably from 30° to 70° C.

Then the organic layer obtained by the washing procedure stated above is distilled, preferably in the presence of an inorganic phosphorus oxyacid such as phosphoric acid, phosphonic acid, phosphinic acid, metaphosphoric acid, pyrophosphoric acid, condensed phosphoric acid, or polyphosphoric acid or an organic phosphorus oxyacid such as phenylphosphonic acid or phenylphosphinic acid. These phosphorus oxyacids can also be used in the form of acid salts. After completion of the wash and prior to the distillation, the phosphorus oxyacid is added in an amount of 0.01 to 10%, preferably 0.05 to 5%, by weight based on the N-substituted maleimide.

The distillation is conducted under normal or reduced pressure. Since N-substituted maleimides have tendencies to polymerize, the distillation is desirably carried out at a temperature as low as possible and hence under a pressure generally up to 20 mm Hg, preferably up to 10 mm Hg.

The constitution and effect of the present invention are illustrated in more detail with reference to the following examples, which are not intended to impose any restriction on the scope of the invention.

EXAMPLE 1

Into a reactor equipped with a thermometer, stirrer dropping funnel, and reflux condenser fitted with a water separator were charged 107.8 g of maleic anhydride, 400 ml of toluene, 25 ml of dimethylformamide, 5.0 g of p-toluenesulfonic acid, 0.1 g of copper sulfate, and 0.2 g of p-methoxyphenol. This mixture was heated with stirring to form a solution. Then 93.1 g of aniline was dropped from the dropping funnel into the solution and reacted under reflux for 3 hours. The water formed during the reaction was removed through the water separator. After ending of the reaction, the reacting product solution was analyzed by gas chromatography, therefrom the formation of 172.1 g of N-phenylmaleimide being confirmed. The reaction yield (conversion to product) was 99.4%.

Then the reaction product solution was cooled to 60° C., 200 g of a 6% aqueous sodium carbonate solution was added and mixed by stirring for 20 minutes, and the resulting mixture was left standing for 20 minutes to separate into two layers, of which the aqueous layer was removed. The obtained organic layer, maintained at 50° C., was washed again with 100 g of dilute sulfuric acid adjusted previously to pH 2, and the resulting aqueous layer was removed. In these two washing operations, no emulsion layer or insoluble matter formed between the organic layer and the aqueous layer and both layers were clear and uniform, after standing thereof. Then 0.5 g of 85% phosphoric acid was added to the separated organic layer, and the solvent was removed by vaporizing at 20–130 mm Hg. The residue was distilled over 3 hours under a vacuum of 9 mm Hg at a bath temperature of 160° C. Thus, 165.2 g of N-phenylmaleimide was obtained (a pale yellow solid, m.p. 89–90° C., yield 95.4%, purity determined by gas chromatography: 99.9%). The amount of still residue from the distillation was 0.8 g.

COMPARATIVE EXAMPLE 1

The procedure of Example 1 was followed except that copper sulfate was not added. The result was that the reaction yield was 96.1% and 129.2 g of N-phenylmaleimide was obtained (a pale yellow solid, m.p. 80–90° C., yield 74.6%, purity determined by gas chromatography: 99.6%). In the washing operation, 15 ml of an emulsion layer containing insoluble matter was formed by the first wash and 120 ml of a similar emulsion layer was formed by the second wash. The amount of still residue was 16.2 g.

COMPARATIVE EXAMPLE 2

The procedure of Example 1 was followed except that neither dimethylformamide nor copper sulfate was added. In this case, a yellow reaction product mixture in slurry form was obtained in a reaction yield of 87.4%, but the next washing operation turned the whole mixture into a liquid in emulsion form containing yellow-white insoluble matter and virtually no aqueous layer separated. Hence the experiment was stopped.

COMPARATIVE EXAMPLE 3

The procedure of Example 1 was followed except that dimethylformamide was not added. The result was that the reaction yield was 87.9% and 104.4 g of N-phenylmaleimide was obtained (a pale yellow solid, m.p. 89–90° C., yield 60.3%, purity 99.8%). In the washing operation, 12 ml of an emulsion layer containing insoluble matter was formed by the first wash and 8 ml of a similar emulsion layer was formed by the second wash. The amount of still residue was 13.0 g.

EXAMPLE 2

Into the same reactor as used in Example 1 were charged 103.0 g of maleic anhydride, 200 ml of xylene, 10 ml of dimethylsulfoxide, 3.0 g of 98% sulfuric acid, 0.05 g of a copper powder, and 0.1 g of hydroquinone. This mixture was heated with stirring to form a solution. Then 93.1 g of aniline was dropped drom the dropping funnel into the solution and reacted under reflux for 2 hours. The water formed during the reaction was removed through the water separator. After ending of the reaction the reaction product solution was analyzed by gas chromatography, therefrom the formation of 170.0 g of N-phenylmaleimide being confirmed. The reaction yield in this case was 98.2%.

Then the reaction product solution was cooled to 50° C., 200 g of a 4.5% aqueous sodium hydroxide solution was added and mixed by stirring for 20 minutes, and the resulting mixture was left standing for 10 minutes to separate into two layers, of which the aqueous layer was removed. The obtained organic layer, maintained at 50° C., was washed again with 100 g of a dilute aqueous phosphoric acid solution adjusted previously to pH 1.5, and the resulting aqueous layer was removed. During these washing and separating operations, the formation of emulsion layer or of insoluble matter was not observed at all. The solvent was removed from the separated organic layer by vaporization under 20–130 mm Hg, and 400 ml of isopropanol heated to 70° C. was added to the residue, dissolving it at 70–75° C. Then the solution was cooled to 10° C. while stirring gently. Precipitated crystals were filtered off, and washed with 100 ml of isopropanol. The mother liquor, i.e. the filtrate, and the washings were combined together, concentrated to a volume of about 50 ml, and cooled again to 10° C. Precipitated crystals were filtered off and washed. These crystals and the formerly obtained crystals were combined together and dried in hot air at 70° C. for 1 hour, yielding 163.1 g of N-phenylmaleimide (a pale yellow solid, m.p. 89–90° C., yield 94.2%, purity 99.9%).

EXAMPLE 3 and 4

Results as shown in Table 1 were obtained by following the procedure of Example 1 except for using each of 127.6 g of o-chloroaniline and 107.2 g of o-toluidine as a primary amine and 0.1 g of cupric oxide as a copper compound and changing the distillation pressure in each case.

TABLE 1

| Example No. | 3 | 4 |
|---|---|---|
| Raw material amine | o-Chloroaniline 127.6 g | o-Toluidine 107.2 g |
| Reaction yield | 98.1% | 95.7% |
| Distillation pressure | 3–4 mm Hg | 7 mm Hg |
| Product | N—o-Chlorophenylmaleimide | N—o-toluylmaldimide |
| Appearance | Pale yellow solid | Pale yellow solid |
| Yield (weight) | 194.7 g | 172.2 g |
| Yield (percentage) | 93.8% | 92.0% |
| M.P. | 73–74° C. | 76–77° C. |
| Purity | 99.7% | 99.8% |
| Amount of still residue | 1.8 g | 2.6 g |

EXAMPLE 5

Into the same reactor as used in Example 1 were charged 107.8 g of maleic anhydride, 400 ml of toluene, 25 ml of dimethylformamide, 50 g of an ion-exchange resin (tradename: Amberist 15, supplied by Rohm & Haas Co.), 0.2 g of copper acetate, and 0.2 g of p-methoxyphenol. This mixture was heated with stirring to form a solution. Then 73.1 g of n-butylamine was dropped from the dropping funnel into the solution and reacted under reflux for 6 hours. The water formed during the reaction was removed through the water separator. After ending of the reaction, the ion-exchange resin catalyst was filtered off and washed with toluene. According to the result of gas chromatographic analysis, the reaction yield was 84.7%.

Then the reaction product solution, maintained at 60° C., was washed twice similarly to Example 1 (once with 300 ml of a 6% aqueous sodium carbonate solution and once with dilute sulfuric acid adjusted to pH 2). During the washing and separating operations, the formation of emulsion layer or of insoluble matter was not observed at all. After addition of 0.5 g of 85% phosphoric acid to the separated organic layer, the solvent was removed by vaporization at 130–20 mm Hg, and the residue was distilled over 3 hours under a vacuum of 6 mm Hg at a bath temperature of 90° C. Thus 123.5 g of N-n-butylmaleimide was obtained (a colorless clear liquid, B.P.

86-89° C./6 mm Hg, yield 80.6%, purity 99.5%). The amount of still residue was 2.8 g.

EXAMPLE 6

Into the same reactor as used in Example 1 were charged 107.8 g of maleic anhydride, 400 ml of toluene, 25 ml of dimethylformamide, 0.1 g of copper sulfate, and 0.2 g of p-methoxyphenol. This mixture was stirred to form a solution. Then 93.1 g of aniline was dropped from the dropping funnel into the solution in 1 hour to react while maintaining the reaction temperature at 40° C. or below, and further the resulting mixture was aged for 1 hour under stirring at 40° C. The resulting slurry of melanilinic acid, after addition of 5.0 g of p-toluenesulfonic acid, was subjected to dehydrating reaction under reflux for 3 hours while removing the formed water through azeotropic distillation. According to the result of gas chromatographic analysis, this reaction yield was 93.5%.

Then the same after-treatment of the obtained reaction product solution as in Example 1 gave 154.4 g of N-phenylmaleimide (a pale yellow solid, m.p. 89-90° C., yield 89.2%, purity 99.8%). In the first and second washing operations, the formation of emulsion layer was not observed at all. The amount of still residue was 1.2 g.

COMPARATIVE EXAMPLE 4

The procedure of Example 6 was followed except that copper sulfate was not added. The result was that the reaction yield was 90.8% and 116.8 g of N-phenylmaleimide was obtained (a pale yellow solid, m.p. 89-90° C., yield 67.5% purity 99.1%). In the washing operation, 60 ml of an emulsion layer containing insoluble matter was formed by the first wash and 120 ml of a similar emulsion layer was formed by the second wash. The amount of still residue was 10.2 g.

EXAMPLES 7-10

Results as shown in Table 2 were obtained by conducting experiments according to the procedure of Example 1 except that copper sulfate was used in different amounts.

TABLE 2

| Example No. | 7 | 8 | 9 | 10 |
|---|---|---|---|---|
| Amount of Cu-sulfate used | 0.01 g | 0.03 g | 0.05 g | 0.2 g |
| Volume of emulsion layer | | | | |
| Wash with dil. alkali | 3 ml | 2 ml | 1 ml | 0 ml |
| Wash with dil. acid | 5 ml | 1 ml | 0 ml | 0 ml |
| N—Phenylmaleimide | | | | |
| Appearance | Yellow solid | Yellow solid | Yellow solid | Yellow solid |
| Yield (weight) | 156.2 g | 162.8 g | 163.7 g | 165.1 g |
| Yield (percentage) | 90.2% | 94.0% | 94.5% | 95.3% |
| M.P. | 88-90° C. | 89-90° C. | 89-90° C. | 89-90° C. |
| Purity | 99.6% | 99.8% | 99.9% | 99.9% |
| Amount of still residue | 8.6 g | 4.5 g | 1.5 g | 1.1 g |

COMPARATIVE EXAMPLES 5-8

Results as shown in Table 3 were obtained by conducting experiments according to the procedure of Example 1 except that t-butylcatechol, phenothiazine, 98% sulfuric acid, and 85% phosphoric acid were used each in place copper sulfate.

TABLE 3

| Comparative Example No. | 5 | 6 | 7 | 8 |
|---|---|---|---|---|
| Additive | t-Butylcatechol | Phenothiazine | 98% $H_2SO_4$ | 85% $H_3PO_4$ |
| Amount used | 0.2 g | 0.2 g | 0.2 g | 0.2 g |
| Volume of emulsion layer | | | | |
| Wash with dil. alkali | 120 ml | 10 ml | 120 ml | 40 ml |
| Wash with dil. acid | 50 ml | 60 ml | 60 ml | 50 ml |
| N—Phenylmaleimide | | | | |
| Appearance | Yellow solid | Brown solid | Yellow solid | Yellow solid |
| Yield (weight) | 102.2 g | 133.2 g | 114.0 g | 118.6 g |
| Yield (percentage) | 59.0% | 76.9% | 65.8% | 68.5% |
| M.P. | 88-90° C. | 88-90° C. | 88-90° C. | 88-90° C. |
| Purity | 99.5% | 99.6% | 99.3% | 99.6% |
| Amount of still residue | 10.2 g | 15.8 g | 12.6 g | 10.8 g |

The following examples illustrate the second aspect of the invention:

The impurities contained in the reaction product solution was removed by the filtration and thereafter thus treated solution was allowed to stand for at least 2 hours in the following Examples wherein neither metallic copper nor copper compound was used.

EXAMPLE 11

Into a reactor equipped with a thermometer, stirrer, dropping funnel, and reflux condenser fitted with a water separator were charged 107.8 g of maleic anhydride, 400 ml of xylene, 25 ml of dimethylformamide, and 5.0 g of p-toluenesulfonic acid. This mixture was heated with stirring to form a solution. Then 93.1 g of aniline was dropped from the dropping funnel into the solution over 1 hour to react and the reaction was further continued for 2 hours under reflux. The water formed during the reaction was removed through the water separator. After ending of the reaction, the reaction product solution (a yellow clear liquid) was analyzed by gas chromatography, therefrom the formation of 166.5 g of N-phenylmaleimide being confirmed (reaction yield 96.1%).

Then the reaction product solution was cooled to 50° C., 200 g of 0.6% aqueous sodium carbonate solution was added to the solution to wash it, and the resulting aqueous layer was separated. The pH of this aqueous layer was 6.8. The obtained organic layer was maintained at 50° C., 150 g of dilute sulfuric acid adjusted previously to pH 2 was added to this layer to wash it, and the resulting aqueous layer was separated. The pH of this aqueous layer was 2.9. The thus obtained organic layer was distilled at temperatures of 60° to 110° C. and pressures of 130 to 20 mm Hg to expel the solvent. The distillation continued further for 3 hours under a vacuum of 9 mm Hg at a bath temperature of 160° C. gave 162.3 g of N-phenylmaleimide (a yellow solid, m.p. 89-90° C., yield 93. Purity determined by gas chromatography: 99.8%). The final distillation left 4.8 g still residue.

COMPARATIVE EXAMPLE 9

The procedure of Example 11 was followed except that the second wash, that is, the wash with dilute sulfuric acid was omitted, whereby 81.6 g of N-phenylmaleimide was obtained (a yellow solid, m.p. 88-90° C., yield 47.1%, purity determined by gas chromatography: 98.6%). The amount of still residue was 88.6 g.

COMPARATIVE EXAMPLE 10

The procedure of Example 11 was followed except that the wash with a dilute aqueous alkali solution (dilute aqueous Na2CO3) was omitted, whereby 123.0 g of N-phenylmaleimide was obtained (a yellow solid, m.p. 88–90° C., yield 71.0%, purity determined by gas chromatography: 98.5%). The amount of still residue was 42.6 g.

COMPARATIVE EXAMPLE 11

The procedure of Example 11 was followed except that pure water was used in place of the dilute aqueous sodium carbonate solution and in place of the dilute surfuric acid, whereby 148.3 g of N-phenylmaleimide was obtained (a yellow solid, m.p. 88–90° C., yield 85.6%, purity determined by gas chromatography: 98.8%). The amount of still residue was 18.8 g.

EXAMPLE 12

The procedure of Example 11 was followed except that 130 g of a 10% aqueous potassium hydroxide solution was used as a dilute aqueous alkali solution and 300 g of a dilute aqueous phosphoric acid solution of pH 2.5 was used as a dilute aqueous acid solution, whereby 160.5 g f N-phenylmaleimide was obtained (a yellow solid, m.p. 88–90° C., yield 92.7%, purity determined by gas chromatography: 99.5%). The amount of still residue was 6.6 g.

EXAMPLE 13 AND 14

Results as shown in Table 4 were obtained by conducting experiments according to the procedure of Example 11 except that 127.6 g of o-chloroaniline and 107.2 g of o-toluidine were used severally as primary amines and the distillation pressure was changed in each case.

TABLE 4

| Example No. | 13 | 14 |
|---|---|---|
| Raw material amine | o-Chloroaniline | o-Toluidine |
| Reaction yield | 95.1% | 92.7% |
| Distillation Pressure | 3–4 mm Hg | 7 mm Hg |
| Product | N—o-Chlorophenyl-maleimide | N—o-Toluyl-maleimide |
| Appearance | Pale yellow solid | Pale yellow solid |
| Yield (weight) | 190.5 g | 168.3 g |
| Yield (percentage) | 91.8% | 89.9% |
| M.P. | 72–74° C. | 76–78° C. |
| Purity | 99.4% | 99.6% |
| Amount of still residue | 9.2 g | 5.9 g |

EXAMPLE 15

Into the same reactor as used in Example 11 were charged 107.8 g of maleic anhydride, 400 ml of toluene, 25 ml of dimethylformamide, and 50 g of an ion-exchange resin (tradename: Amberist 15, supplied by Rohm & Haas Co.). This mixture was heated with stirring to form a solution.

Then 73.1 g of n-butylamine was dropped from the dropping funnel into the solution over 1 hour to react, and the reaction was further continued for 5 hours under reflux. The water formed during the reaction was removed through the water separator. After ending of the reaction, the reaction product solution was cooled to 60° C., and the catalyst (ion-exchange resin) was filtered and washed with toluene. This reaction product solution was analyzed by gas chromatography, therefrom the formation of 120.1 g of N-n-butylmaleimide being confirmed (reaction yield 78.4%).

Then the reaction product solution, maintained at 60° C., was washed with 250 g of a 6% aqueous sodium carbonate solution, and the resulting aqueous layer was separated. The pH of this aqueous layer was 5.2. The obtained organic layer maintained at 60° C., was washed again by adding 100 g of a dilute aqueous phosphoric acid solution adjusted previously to pH 1.5, and the resulting aqueous layer was separated. The pH of this aqueous layer was 2.0. The thus obtained organic layer was distilled at temperatures of 60 to 110° C. and pressures of 130 to 20 mm Hg to remove the solvent. The distillation further continued for 3 hours under a vacuum of 6 mm Hg at a bath temperature of 90° C. gave 115.6 g of N-n-butylmaleimide (a colorless clear liquid, b.p. 86–89°C./6 mm Hg, yield 75.5%, purity determined by gas chromatography: 99.0%). The amount of still residue was 8.6 g.

EXAMPLE 16

Into a reactor equipped with a thermometer, stirrer, dropping funnel, and reflux condenser fitted with a water separator were charged 107.8 of maleic anhydride, 400 ml of xylene, 25 ml of dimethylformamide, and 5.0 g of p-toluenesulfonic acid. This mixture was heated with stirring to form a solution. Then 93.1 g of aniline was dropped from the dropping funnel into the solution over 1 hour to react. The reaction under reflux was continued for 2 further hours. The water formed during the reaction was removed through the water separator. After ending of the reaction, the reaction product solution was analyzed by gas chromatography, therefrom the formation of 167.1 g of N-phenylmaleimide being confirmed (reaction yield 96.5%).

Then the reaction product solution, cooled to 50° C., was washed by adding 200 g of a 6% aqueous sodium carbonate solution, and the resulting aqueous layer was separated. The pH of this aqueous layer was 6.9. The obtained organic layer, after addition of 0.5 g of 85% phosphoric acid, was distilled at temperatures of 60 to 110° C. and pressures of 130 to 20 mm Hg to remove the solvent. The distillation was continued for 3 further hours under a vacuum of 9 mm Hg at a bath temperature of 160° C., yielding 160.6 g of N-phenylmaleimide (a yellow solid, m.p. 89–90° C., yield 92.7%, purity determined by gas chromatography: 99.4%). The amount of still residue was 7.3 g.

COMPARATIVE EXAMPLES 12–15

Results as shown in Table 5 were obtained by conducting experiments according to the procedure of Example 16 except that p-methoxyphenol, phenothiazine, 1 98% sulfuric acid, and terephthalic acid were used each in place of the 85% phosphoric acid.

TABLE 5

| Comparative Example No. | 12 | 13 | 14 | 15 |
|---|---|---|---|---|
| Additive | p-Methoxyphenol | Phenothiazine | 98% H2SO4 | Terephthalic acid |
| Amount used | 0.5 g | 0.5 g | 0.5 g | 0.5 g |
| N—Phenylmaleimide | | | | |
| Appearance | Yellow solid | Brown solid | Yellow solid | Yellow solid |
| Yield (weight) | 89.0 g | 75.5 g | 56.3 g | 124.0 g |

TABLE 5-continued

| Comparative Example No. | 12 | 13 | 14 | 15 |
|---|---|---|---|---|
| Yield (percentage) | 51.4% | 43.6% | 32.5% | 71.6% |
| M.P. | 88–90° C. | 88–90° C. | 87–90° C. | 88–90° C. |
| Purity | 97.6% | 98.4% | 97.3% | 98.9% |
| Amount of still residue | 81.9 g | 95.1 g | 112.8 g | 46.3 g |

EXAMPLES 17 and 18

Results as shown in Table 6 were obtained by conducting experiments according to the procedure of Example 16 except that 0.5 g of phosphonic acid and 1.0 g of phenyl phosphonic acid were used each as a phosphorus oxyacid in the distillation.

TABLE 6

| Example No. | 17 | 18 |
|---|---|---|
| Phosphorus oxyacid | Phosphonic acid | Phenylphosphonic acid |
| Amount used | 0.5 g | 1.0 g |
| N—phenylmaleimide | | |
| Appearance | Yellow solid | Yellow solid |
| Yield (weight) | 159.2 g | 156.8 g |
| Yield (percentage) | 91.9% | 90.5% |
| M.P. | 88–90° C. | 88–90° C. |
| Purity | 99.2% | 99.0% |
| Amount of still residue | 7.6 g | 10.3 g |

EXAMPLE 19

According to procedure of Example 16, maleic anhydride was imidized by dehydrating reaction and the reaction product solution was washed with a dilute aqueous alkali solution. The thus obtained organic layer, maintained at 50° C., was washed again with 100 g of dilute sulfuric acid adjusted previously to pH 2, and the resulting aqueous layer was separated. The pH of this aqueous layer was 3.1.

Then the obtained organic layer, after addition of 0.2 g of 85% phosphoric acid, was distilled at temperatures of 60° to 110° C. and pressures of 130 to 20 mm Hg to remove the solvent. The distillation was further continued for 3 hours under a vacuum of 9 mm Hg at a bath temperature of 160° C., yielding 163.1 g of N-phenylmaleimide (a yellow solid, m.p. 89–90° C., yield 94.2%, purity determined by gas chromatography: 99.9%). The amount of still residue was 1.8 g.

EXAMPLES 20 and 21

Results as shown in Table 7 were obtained by conducting experiments according to the procedure of Example 16 except that 127.6 g of o-chloroaniline and 107.2 g of o-toluidine were used severally as primary amines and the distillation pressure was changed in each case.

TABLE 7

| Example No. | 20 | 21 |
|---|---|---|
| Raw material amine | o-Chloroaniline | o-Toluidine |
| Reaction yield | 95.5% | 92.3% |
| Distillation pressure | 3–4 mm Hg | 7 mm Hg |
| Product | N—o-Chlorophenylmaleime | N—o-Toluylmaleimide |
| Appearance | Pale yellow solid | Pale yellow solid |
| Yield (weight) | 191.2 g | 167.6 g |
| Yield (percentage) | 92.1% | 89.5% |
| M.P. | 72–74° C. | 76–78° C. |

TABLE 7-continued

| Example No. | 20 | 21 |
|---|---|---|
| Purity | 99.3% | 99.4% |
| Amount of still residue | 8.7 g | 10.6 g |

EXAMPLE 22

Into the same reactor as used in Example 16 were charged 107.8 g of maleic anhydride, 400 ml of toluene, 25 ml of dimethylformamide, and 50 g of an ion-exchange resin (tradename: Amberist 15, supplied by Rohm & Haas Co.). This mixture was heated with stirring to form a solution.

Then 73.1 g of n-butylamine was dropped from the dropping funnel into solution in 1 hour to react and the reaction under reflux was continued for 5 further hours. The water formed during the reaction was removed through the water separator. After ending of the reaction, the reaction product solution was cooled to 60° C. and the catalyst was filtered and washed with toluene. This reaction product solution (a pale brown liquid) was analyzed by gas chromatography, therefrom the formation of 117.8 g of N-n-butylmaleimide being confirmed (reaction yield 76.9%).

Then the reaction product solution, maintained at 60° C., washed with 250 g of a 6% aqueous sodium carbonate solution, and the resulting aqueous layer was separated. The pH of this aqueous layer was 5.2. The obtained organic layer, maintained at 60° C., was washed again with 100 g of a dilute aqueous phosphoric acid solution adjusted previously to pH 1.5, and the resulting aqueous layer was separated. The pH of this aqueous layer was 2.0. The obtained organic layer, after addition of 0.4 g of 85% phosphoric acid, was distilled at temperatures of 60° to 110° C. and pressures of 130 to 20 mm Hg to expel the solvent. The distillation was continued for 3 further hours under a vacuum of 6 mm Hg at a bath temperature of 90° C., yielding 114.1 g of N-n-butylmaleimide (a colorless clear liquid, b.p. 86–89°C./6 mm Hg, yield 74.5%, purity determined by gas chromatography: 99.2%). The amount of still residue was 4.5 g.

EXAMPLES 23 and 24

Results as shown in Table 8 were obtained by conducting experiments according to the procedure of Example 16 except that in the washing operations, 200 g of dilute sulfuric acid of pH 3 and 200 g of water were used severally as wash liquids.

TABLE 8

| Example No. | 23 | 24 |
|---|---|---|
| Wash liquid | Dilute sulfuric acid, pH 3, 200 g | Water, 200 g |
| N—Phenylmaleimide | | |
| Appearance | Yellow solid | Yellow solid |
| Yield (weight) | 156.3 g | 158.3 g |
| Yield (percentage) | 90.2% | 91.4% |
| M.P. | 88–90° C. | 88–90° C. |
| Purity | 99.0% | 99.2% |
| Amount of still residue | 12.9 g | 10.2 g |

EXAMPLES 25–28

Results as shown in Table 9 were obtained by conducting experiments according to the procedure of Example 16 except that the amount of 85% phosphoric acid used in the distillation was changed.

TABLE 9

| Example No. | 25 | 26 | 27 | 28 |
|---|---|---|---|---|
| Amount of 85% phosphoric acid used N—Phenylmaleimide | 0.1 g | 0.3 g | 1 g | 5 g |
| Appearance | Yellow solid | Yellow solid | Yellow solid | Yellow solid |
| Yield (weight) | 149.8 g | 160.0 g | 159.0 g | 153.5 g |
| Yield (percentage) | 86.5% | 92.4% | 91.8% | 88.6% |
| M.P. | 88–90° C. | 89–90° C. | 89–90° C. | 88–90° C. |
| Purity | 99.2% | 99.4% | 99.5% | 99.1% |
| Amount of still residue | 21.8 g | 7.2 g | 8.6 g | 16.5 g |

According to the first aspect of the present invention, N-substituted maleimides of high purity can be obtained in high yields. The invention in the first aspect has advantages as following:

(i) In the washing step, the separability of product mixture is markedly improved and the workability thereof is also improved.

(ii) Yields of product from the reaction and from the purification are increased.

(iii) The purity of product is improved.

(iv) The purification is easy since by-product formation is minimized.

(v) The polymerization of product in the purification can be prevented.

According to the second aspect of the present invention, N-substituted maleimides of at least about 99% purity can be obtained in about 90% and more purification yields the invention in the second aspect has advantages of as following:

(i) The distillation yield of product is markedly increased.

(ii) The polymerization of product during the distillation can be prevented.

(iii) The amount of still residue after product distillation can be remarkably reduced.

(iv) The product purity is elevated.

What is claimed is:

1. A process for producing N-substituted maleimides, which comprises:
    (1) synthesizing an N-substituted maleimide by reacting maleic anhydride with an amine selected from the group consisting of aromatic primary amines and aliphatic primary amines in the presence of a catalyst which promotes the formation of N-substituted maleimide and of at least one member selected from the group consisting of metallic copper and copper compounds, and
    (2) purifying the N-substituted maleimide product of step (1) by (i) washing the N-substituted maleimide-containing reaction product mixture with at least one liquid selected from a dilute aqueous alkali solution, water, and a dilute aqueous acid solution, and (ii) isolating the N-substituted maleimide from the washing organic layer.

2. The process of claim 1, wherein the step of synthesizing an N-substituted maleimide comprises the imidization of maleic anhydride in one stage and the isolation in the purification step is carried out by distillation.

3. The process of claim 1, wherein the washing in the purification step comprises the wash with a dilute aqueous alkali solution and the subsequent wash with a dilute aqueous acid solution.

4. The process of claim 2, wherein the isolation by distillation in the purification step is carried out in the presence of a phosphorus oxyacid.

5. The process of claim 1, wherein the step of synthesizing an N-substituted maleimide comprises synthesizing a maleic acid monoamide and then subjecting it to dehydration ring closure and the isolation in the purification step is carried out by distillation.

6. The process of claim 5, wherein the washing in the purification step comprises the wash with a dilute aqueous alkali solution and the subsequent wash with a dilute aqueous acid solution.

7. The process of claim 5, wherein the isolation by distillation in the purification step is carried out in the presence of a phosphorus oxyacid.

8. A process for purifying N-substituted maleimides which comprises steps of
    washing an N-substituted maleimide-containing reaction product mixture resulting from reacting maleic anhydride with an aromatic or aliphatic primary amine, with at least one liquid selected from a dilute aqueous alkali solution, water, and a dilute aqueous acid solution, and
    isolating the maleimide from the resulting organic layer.

9. The purification process of claim 8, wherein the step of isolating the maleimides from the organic layer is operated by distillation in the presence of a phosphorus oxyacid.

10. The purification process of claim 8, wherein the step of washing comprises the wash with a dilute aqueous alkali solution and the subsequent wash with a dilute aqueous acid solution.

11. The process of claim 1, wherein said catalyst is an inorganic acid, an organic acid, an organic base or an ion exchange resin.

12. The process of claim 11, wherein said inorganic acid is sulfuric acid, sulfurous acid, sulfuric anhydride, phosphoric acid, phosphorous acid or polyphosphoric acid; said organic acid is benzenesulfonic acid, trichloroacetic acid, toluenesulfonic acid, benzenephosphonic acid or trifluoroacetic acid; said organic base is triethylamine, pyridine, dimethylaniline or sodium acetate; and said ion exchange resin is a strong acid ion exchange resin, a weak acid ion exchange resin or a weak base ion exchange resin.

13. The process of claim 1, wherein the amount of catalyst employed ranges from 0.05 to 40% by weight based on the reaction fluid.

* * * * *